United States Patent [19]
Daniels

[11] 3,985,727
[45] Oct. 12, 1976

[54] AMINOGLYCOSIDE ANTIBIOTICS
[75] Inventor: Peter J. L. Daniels, Cedar Grove, N.J.
[73] Assignee: Schering Corporation, Kenilworth, N.J.
[22] Filed: Mar. 28, 1975
[21] Appl. No.: 563,046

[52] U.S. Cl. .................................... 536/17; 536/4; 536/18; 536/53
[51] Int. Cl.² ........................................ C07H 15/22
[58] Field of Search ....... 260/210 AB, 210 K, 210 R

[56] References Cited
UNITED STATES PATENTS
3,780,018   12/1973   Konishi et al. .............. 260/210 AB OTHER PUBLICATIONS
Umezawa et al. "The Jour. of Antibiotics", vol. XXV, No. 12, 1972, pp. 743–745.
Mallams et al. "The Jour. of Antibiotics", vol. XXVI, No. 12, 1973, pp. 782–783.

*Primary Examiner*—Johnnie R. Brown
*Attorney, Agent, or Firm*—Raymond A. McDonald; Stephen B. Coan

[57] ABSTRACT

This disclosure relates to the preparation of certain gentamine derivatives, to their use as intermediates in the preparation of certain novel pseudotrisaccharides containing a gentamine moiety, and to the use of these pseudotrisaccharides as antibacterial agents.

20 Claims, No Drawings

AMINOGLYCOSIDE ANTIBIOTICS

In one aspect of this invention, this application relates to novel pseudotrisaccharides, their pharmaceutically acceptable acid addition salts and Schiff's base oxazolidine derivatives, and to the use of such compounds as antibacterial agents.

In another aspect of this invention, this application relates to certain gentamine derivatives, to processes for their obtention and to their conversion of pseudotrisaccharides. In still another aspect of this invention, this application relates to the preparation of certain monosaccharides, and derivatives thereof, and to the use of such compounds in the preparation of pseudotrisaccharides.

More particularly, this invention, in its composition of matter aspect, relates to novel pseudotrisaccharides of the formula:

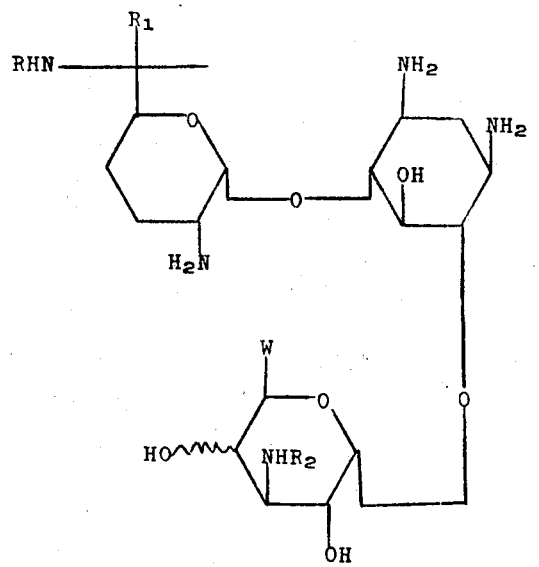

I and their pharmaceutically acceptable acid addition salts, wherein each of R and $R_1$ represent hydrogen or methyl, $R_2$ is hydrogen or lower alkyl having less than 5 carbon atoms, and W represents hydrogen, methyl or hydroxymethyl.

Representative of the lower alkyl radicals having 1 to 4 carbon atoms include ethyl, propyl, isopropyl, n-butyl, i-butyl, sec.-butyl or tert.-butyl with methyl being preferred. Suitable pharmaceutically acceptable acid addition salts are those art recognized salts prepared from well known acids which include those acids which are known to have been used with the class of pseudotrisaccharide to which the compounds of this invention pertain. However, those salts formed from inorganic acids, such as hydrochloric acid, hydrobromic acid, and sulfuric acid are most preferred.

As can be seen upon visual inspection, the gentamines, i.e. gentamine $C_1$, gentamine $C_2$, gentamine $C_{1a}$ and gentamine $C_{2b}$, are the pseudodisaccharides common to the pseudotrisaccharides (I) of this invention. These gentamines are represented by the structural formula:

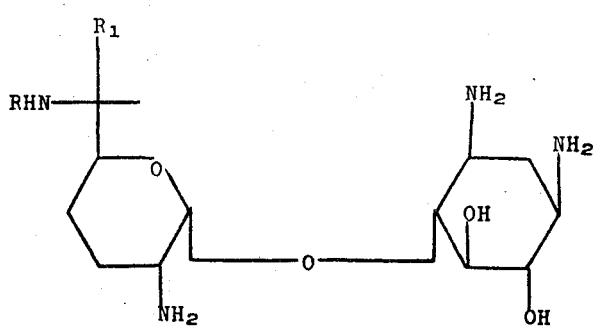

II wherein for gentamine $C_1$, R and $R_1$ are both methyl, for gentamine $C_2$, $R_1$ is methyl and R is hydrogen, for gentamine $C_{1a}$, R and $R_1$ are both hydrogen, and for gentamine $C_{2b}$, R is methyl and $R_1$ is hydrogen.

The preparation of the pseudotrisaccharides of formula I is effected by condensation procedures wherein certain gentamine derivatives are caused to react with an appropriately substituted pyranosyl monosaccharide derivative to produce a "blocked" or "protected" pseudotrisaccharide which is readily converted to the desired pseudotrisaccharides of formula I.

In general, the condensation reactions suitable for preparing the desired pseudotrisaccharides are the Lemieux reaction, the Koenigs-Knorr reaction, and a halide ion catalyzed procedure all of which are known to those of ordinary skill in the art. The utilization of the foregoing glycosylation procedures employ selectively blocked monosaccharides and selectively blocked pseudodisaccharides.

Suitable selectively blocked gentamine derivatives useful for producing the desired compounds of formula I are represented by the formula:

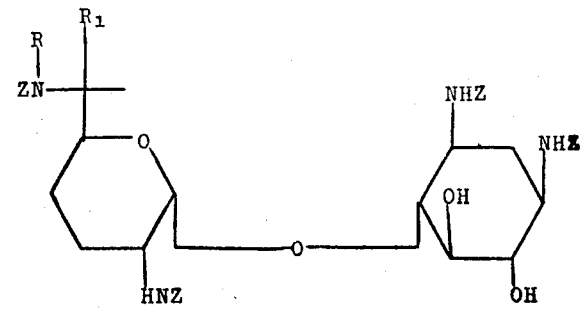

IIa wherein R and $R_1$ are hydrogen or methyl and each Z is an amino protective group. The term "amino protective group" is well-known in organic chemistry and refers to a large number of groups suitable for temporarily blocking (synonymous with protecting) an amino moiety in a molecule from undergoing chemical reactions, yet are readily removed after a desired chemical reaction is effected at other sites of the molecule. Exemplifying these groups are unsubstituted, as well as functionally substituted acyl, alkoxycarbonyl, and arylalkoxycarbonyl groups. These groups are defined in accordance with their standard art recognized meaning as set forth in standard chemical references, (e.g. *Advances in Organic Chemistry*, Methods and Results, Raphael, R. A., Taylor, E.C. and Wynberg, H., Vol. 3, Interscience Publishers, New York, 1963, pp. 159–162, 191–193). Commonly used amino protective groups are such specific acyl groups as acetyl, propionyl and benzoyl groups. Specific alkoxycarbonyl groups are methoxycarbonyl, ethoxycarbonyl, and t-butoxycarbonyl groups. Exemplifying the arylalkoxycarbonyl groups are benzyloxycarbonyl, and 4-methoxybenzyloxy carbonyl groups. Particularly preferred are benzyloxycarbonyl, methoxycarbonyl, ethoxycarbonyl or acetyl groups.

The desired gentamines $C_1$, $C_2$, $C_{1a}$ and $C_{2b}$, of formula II are prepared by methanolysis of gentamicins $C_1$, $C_2$, $C_{1a}$ and $C_{2b}$, respectively, as described by: D. J. Cooper, M. D. Yudis, R. D. Guthrie and A. M. Prior, *J. Chem. Soc.* (C) 960 (1971) and J. B. Morton, R. C. Long, P. J. L. Daniels, R. W. Tkach and J. H. Goldstein, *J. Am. Chem. Soc.*, 95, 7464 (1973). The gentamines, i.e. gentamine $C_1$, gentamine $C_2$, gentamine $C_{1a}$, and gentamine $C_2b$ are converted to their respective tetra-N-protected derivatives (IIa) for use in the desired glycosylation reactions by any one of a variety of methods known in the art. Techniques for preparing the tetra-N-protected gentamines are exemplified in *J. Chem. Soc.* (C) 3126 (1971) and in *Chem. Comm.*, 675, (1973), wherein tetra-N-acetylgentamine $C_1$ and tetra-N-benzyloxycarbonyl gentamine $C_1$ are prepared. Of course, the other tetra-N-acetylgentamines and tetra-N-benzyloxycarbonyl gentamines are prepared by identical procedures. Preparations of other tetra-N-protected gentamines are also effected by standard techniques well-known in the art.

The additional sugar moieties which, together with the previously described gentamines make up the pseudotrisaccharides of this invention are 3-amino-3-deoxy-monosaccharides of the formula:

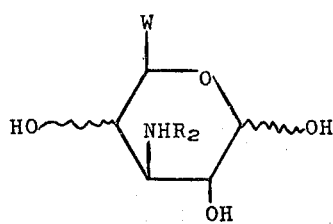

III wherein $R_2$ is hydrogen or lower alkyl having less than 5 carbon atoms, and W is hydrogen, methyl or hydroxymethyl, the wavy lines denoting that the substituent may be in either of its stereoisomeric forms.

The 3-amino-3-deoxypentoses and hexoses used in this work are mostly known in the art. They may be converted to their methyl glysocide N-acetyl derivatives, starting materials for the processes of this invention, by well known methods. For example, methyl 3-acetamido-3,6-dideoxy-β-L-galactopyranoside has been synthesized by Richardson [Carbohydrate Research 4, 415 (1967)]. The corresponding α-D-compound, a starting material for this invention is made by the exactly analogous process form methyl 6-deoxy-α-D-glucopyranoside. The known and analogously known procedures may also be applied to obtain the desired starting 3-amino-3-deoxy monosaccharides of formula III.

The foregoing 3-amino-3-deoxy sugars (III) must be suitably prepared for the glycosylation procedures so that the reaction takes place only at the desired site, i.e. only at those reactive sites which are not "blocked" or otherwise rendered unreactive. In essence, these "blocked" compounds are of the formula:

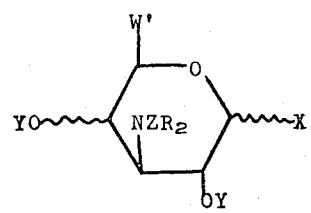

IIIa wherein Y is an appropriate hydroxy blocking group, $R_2$ is hydrogen or a lower alkyl radical, W' is hydrogen, methyl or $CH_2OY$ and X is a suitable leaving group, preferably chlorine or bromine, and Z is as previously defined.

In general, the term "hydroxy protective groups" also is a well known term in the art and refers to those groups suitable for temporarily blocking and thereby protecting a hydroxy moiety in a molecule from undergoing chemical reactions, yet are readily removable after a desired chemical reaction is effected in other sites in the molecule. Exemplifying these groups are unsubstituted, as well as functionally substituted arylalkyl, acyl, alkoxycarbonyl, and aralkoxycarbonyl groups. Common examples of hydroxy protective groups are benzyl, p-nitrobenzoyl, or acetyl. The preferred appropriate hydroxy blocking group for the Koenigs-Knorr and the halide ion reaction procedures is benzyl and for the Lemieux reaction the acetate and the benzoyl groups are preferred.

In those instances wherein the glycosylation reaction employs the Knoenigs-Knorr technique, the blocked monosaccharides (IIIa, Y=benzyl) are suitable for use directly. In effecting the Koenigs-Knorr technique the reaction of the suitably blocked gentamine and the suitably blocked 3-amino-3-deoxy sugar derivatives is usually carried out in the presence of a heavy metal ion, e.g. such salts of mercury and silver as mercuric cyanide, mercuric bromide, silver carbonate, silver oxide, silver perchlorate or silver tosylate. The reaction may be conducted in the presence of an acid aceeptor such as collidine, mercuric oxide or silver oxide. Also, the reaction may be conducted in the presence of a drying agent such as calcium sulfate. Suitable organic solvents for conducting the Koenigs-Knorr reaction include dioxane, tetrahydrofuran, acetonitrile, nitromethane, toluene, benzene or dimethylformamide. The reaction is generally conducted at temperatures from about room temperature to about solvent-reflux temperature.

In those instances wherein the glycosylation process is via the Lemieux reaction, then the monosaccharide reactants of formula IIIa are first converted to a corresponding glycal which is then converted to the required nitroso dimer. The preparation of the glycal and of the nitroso dimer also is effected by techniques well known in the art and may be typified by the following schematic representation:

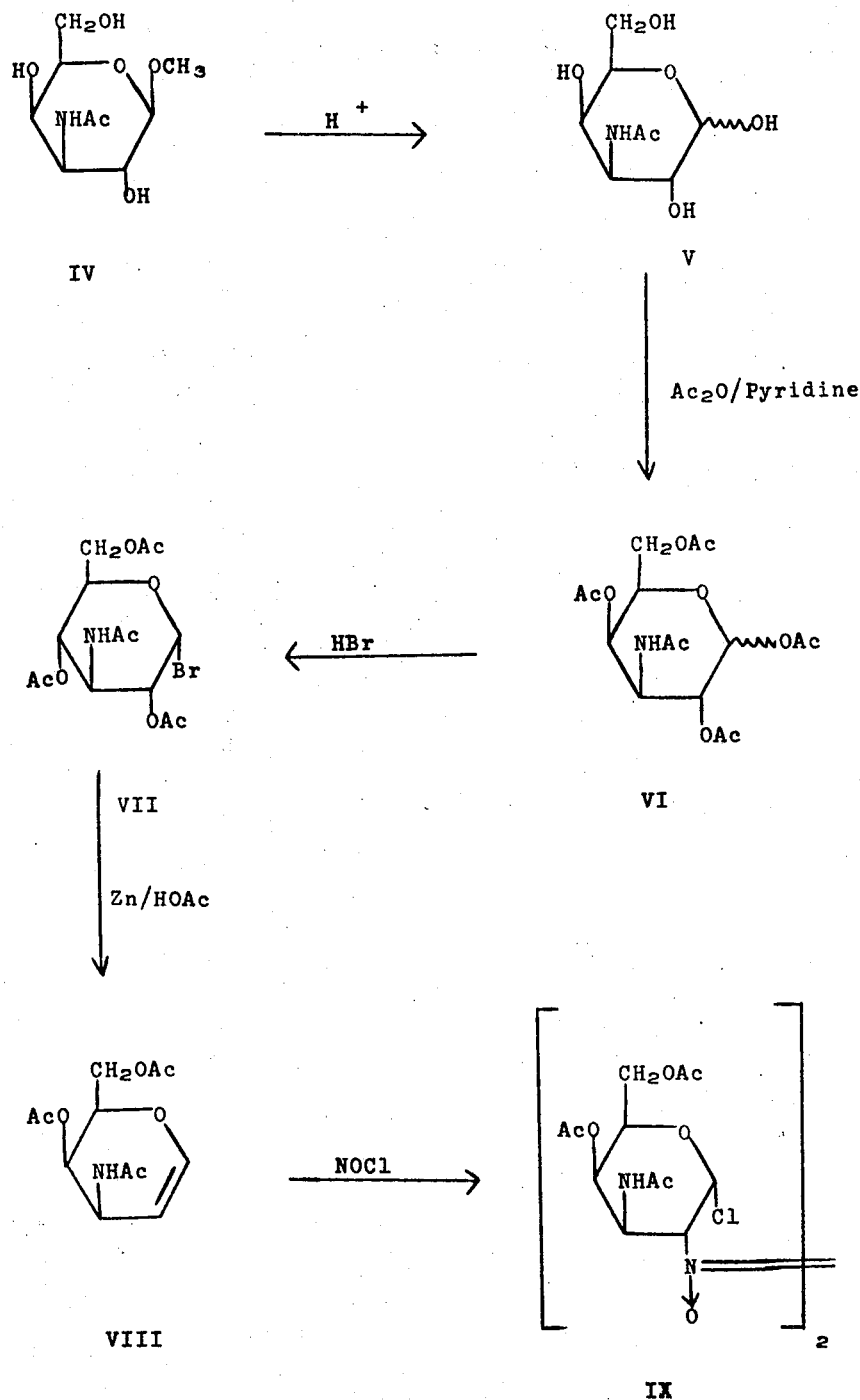

The nitroso dimers (as exemplified by IX) are reacted with the protected gentamine according to the known lemieux reaction conditions to produce oximes (X) which are subjected to oxime exchange reactions to give ketones which are chemically reduced and the final products obtained by standard deblocking techniques. Exemplary of such Lemieux techniques is the following reaction schematic representation:

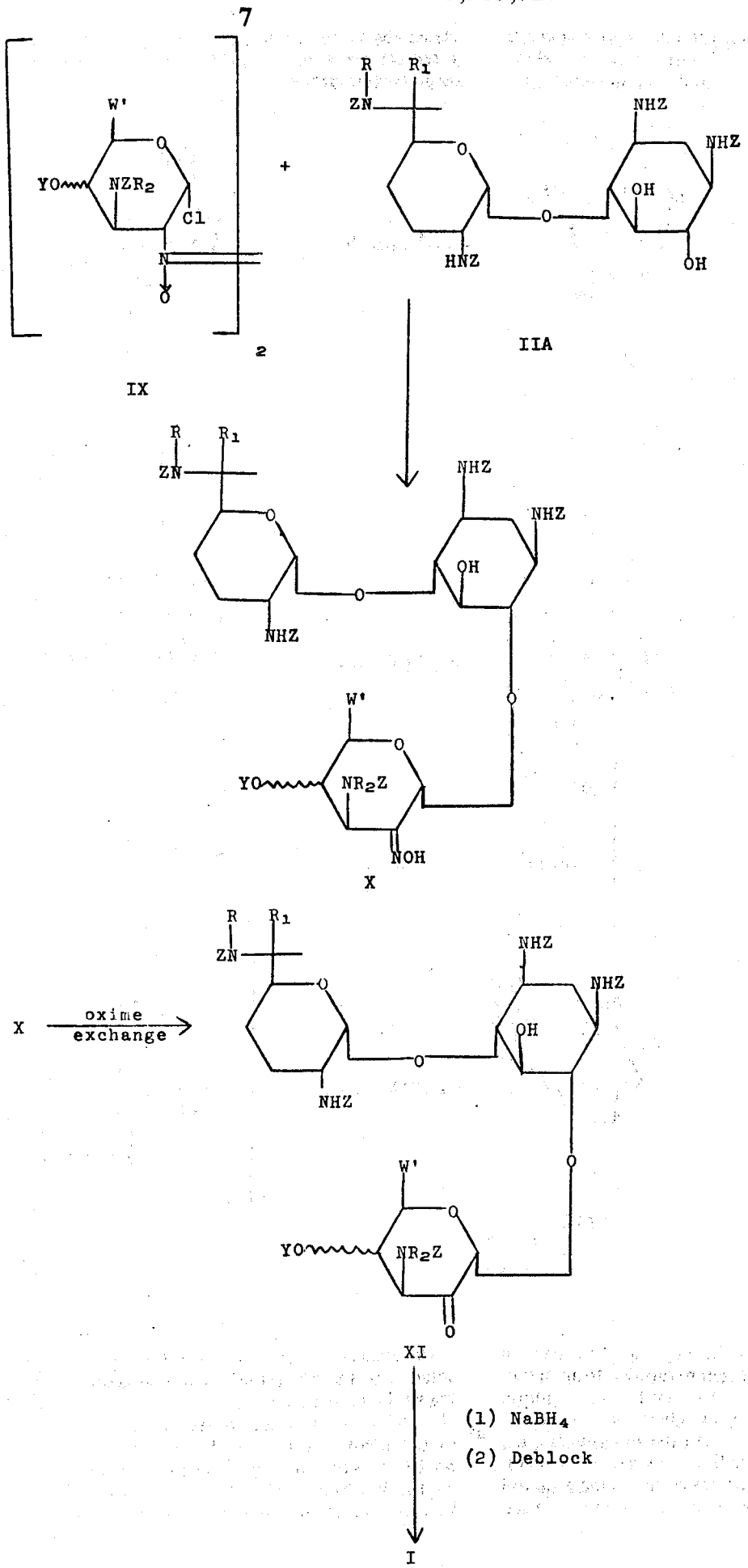

In the foregoing glycoside forming processes the desired 6-0-glycosyl products predominate possibly because of less steric hindrance at position 6. Indeed, the desired 6-0-glycosyl product is almost exclusively produced by the Koenigs-Knorr reaction whilst the desired 6-0-glycosyl product is predominantly produced by the Lemieux reaction. In those instances wherein both the 5-0-glycosyl product and the desired 6-0-glycosyl product is produced then separation of the isomers is readily effected by standard chromatographic techniques.

The elimination of all protective groups present in a pseudotrisaccharide can be effected according to standard procedures, such as hydrolysis, preferably in an alkaline medium, reductive cleavage, such as by hydrogenolysis or by alkali metal-ammonia reductions or by means of hydrazine. Alkaline hydrolysis is preferably effected in reaction mixtures containing an alkali metal hydroxide, e.g. sodium hydroxide. As is to be noted from the hereinafter exemplified procedures, the blocked pseudotrisaccharides may be deblocked in stages. For example, the blocked pseudotrisaccharides may be first treated with sodium in liquid ammonia to partially remove the protective groups and then the product of that reaction is fully deprotected by reaction with sodium hydroxide.

If the final compound desired is prepared from an oximino-group containing intermediate, the oximino group is converted into a keto group and the keto group subsequently can be converted into the hydroxy group. Conversion of the oximino group is preferably effected by means of levulinic acid, titanium trichloride or thallium (III) nitrate and the reduction of the keto group is suitably effected with an alkali metal borohydride, e.g. sodium borohydride The following examples illustrate the preparation of the intermediates and final compounds of this invention.

PREPARATION OF MONOSACCHARIDE INTERMEDIATES

EXAMPLE 1:
Methyl-3-acetamido-3-deoxy-2,4,6-tri-O-benzyl-β-D-galactopyranoside Dissolve 15 g. of methyl 3-acetamido-3-deoxy-β-D-galactopyranoside in DMF (300 ml.). To the solution add barium oxide (111 g.) and barium hydroxide (51 g.) and cool to 0°. With rapid stirring add benzyl bromide (150 ml.) dropwise. Allow the mixture to stir for a further 4 hours at 0° and then 16 hours at room temperature. Dilute the reaction mixture with 750 ml. of chloroform and filter. Concentrate the filtrate at 60° in vacuo to a yellow syrup, and extract this syrup with 500 ml of ethyl acetate. Filter the extract and concentrate in vacuo to a residue. Dissolve the residue in chloroform (200 ml.), wash the solution with 3 × 100 ml. of water then dry the chloroform phase over $MgSO_4$. Remove the $MgSO_4$ by filtration, then add hexane to the filtrate till crystals appear. After standing to complete the crystallization, filter off the product and dry to obtain methyl 3-acetamido-3-deoxy-2,4,6-tri-O-benzyl-β-D-galactopyranoside, 29.53 g. m.p. 147°–151°, $[\alpha]_d^{26}$ +52.5°.

Analysis Found: C, 71.20; C, 6.85; N, 2.66. $C_{30}H_{35}NO_6$ requires C, 71.29; H, 6.93; N, 2.77%.

EXAMPLE 2:
3-Acetamido-3-deoxy-2,4,6-tri-O-benzyl-D-galactopyrawosyl acetate Dissolve 5.0 g. of methyl 3-acetamido-3-deoxy-2,4,6-tri-O-benzyl-β-D-galactopyranoside in a mixture of glacial acetic acid (120 ml.) and 2N sulfuric acid (30 ml.). Heat the solution on the steam bath for 6 hours, cool, and pour into 4 liters of water. Collect the white precipitate by filtration, dissolve in methanol (200 ml.) and slowly add hexane until precipitation is largely complete. Recover the product by filtration (4.0 g., m.p. 165°–167°).

Dissolve 3.0 g. of the aforementioned product in a mixture of acetic anhydride (20 ml.) and pyridine (20 ml.). Allow this mixture to stand for 16 hours then evaporate to a residue in vacuo. Dissolve the residue in chloroform and add isopropanol to incipient turbidity. Allow the product to crystallize. Recover the product by filtration to obtain the title compound of this example. Yield 2.53 g., m.p. 147°–148°.

Analysis Found: C, 69.70; H, 6.83; N, 2.34. $C_{31}H_{35}NO_7$ requires C, 69.79; H, 6.57; N, 2.63%.

EXAMPLE 3:
3-Acetamido-3-deoxy-2,4,6-tri-O-benzyl-α-D-galactopyranosyl chloride Dissolve 1.5 g. of 3-acetamido-3-deoxy-2,4,6-tri-O-benzyl-D-galactopyranosyl acetate in 75 ml. of dioxane containing 4% by weight of hydrogen chloride and add 35 ml. of acetyl chloride to the solution. Allow the mixture to stand in a dry nitrogen atmosphere for 16 hours at 40°. Evaporate the mixture to dryness in vacuo to a syrup. Repeatedly co-distil this residue with dry toluene until all hydrogen chloride is removed. Crystallize the resultant residue with hexane to obtain the title product of this example. Yield 1.1 g., m.p. 158°–159° (decomp.), $[\alpha]_D^{26}$ + 169.9°.

Analysis Found: C, 67.83; H, 6.46; N, 2.62; Cl, 7.23. $C_{29}H_{32}NO_5Cl$ requires C, 68.30; H, 6:28; N, 2.75; Cl, 6.97%.

EXAMPLE 4: Methyl
3-(N-methylacetamido)-3-deoxy-2,4,6-tri-O-benzyl-β-D-galactopyranoside Dissolve methyl 3-acetamido-3-deoxy-2,4,6-tri-O-benzyl-β-D-galactopyranoside (5.05 g.) in dry DMF (100 ml.). With stirring in an atomsphere of dry nitrogen add 0.25 g. of sodium hydride and allow the mixture to stir for 1 hour. Add methyl iodide (2.0 g.) and continue stirring at room temperature for 16 hours. Evaporate the mixture in vacuo to ca 10 ml. then dilute with chloroform. Cautiously add water and shake, separate the layers and re-extract the chloroform layer 3 times with water. Dry the chloroform solution and evaporate to 50 ml. Add hexane to precipitate the title product of this example. Yield ca 4.7 g.

By use of the foregoing types of procedures using the appropriate starting materials, there is produced:

3-(N-methylacetamido)-3-deoxy-2,4,6-tri-O-benzyl-α-D-galactopyranosyl chloride,
3-acetamido-3-deoxy-2,4,6-tri-O-benzyl-α-D-glucopyranosyl chloride,
3-(N-methylacetamido)-3-deoxy-2,4,6-tri-O-benzyl-α-D-glucopyranosyl chloride,
3-acetamido-2,4-di-O-benzyl-3-deoxy-α-D-fucoyranosyl chloride,
3-acetamido-3,6-dideoxy-2,4,-di-O-benzyl-α-D-glucopyranosyl chloride,
3-(N-methylacetamido)-3,6-dideoxy-2,4-di-O-benzyl-α-D-glucopyranosyl chloride,
3-(N-methylacetamido)-2,4-di-O-benzyl-3-deoxy-α-D-fucopyranosyl chloride,
3-acetamido-2,4-di-O-benzyl-3-deoxy-α-D-xylopyranosyl chloride,
3-(N-methylacetamido)-2,4-di-O-benzyl-3-deoxy-α-D-xylopyranosyl chloride,
3-acetamido-2,4-di-O-benzyl-3-deoxy-β-L-arabinopyranosyl chloride,
3-(N-methylacetamido)-2,4-di-O-benzyl-3-deoxy-β-L-arabinopyranosyl chloride.

PREPARATION OF FINAL COMPOUNDS

EXAMPLE 5:

O-[3-Amino-3-deoxy-α-D-glucopyranosyl-(1 → 6)] gentamine $C_1$ 1,3,2',6'-Tetra-N-benzyloxycarbonylgentamine $C_1$ (4.3 gm.) and anhydrous silver p-toluenesulphonate (2.8 gm.) were stirred in dry benzene (250 ml.) and the volume was reduced to 150 ml. by distillation. 3-Acetamido-2,4,6-tri-O-benzyl-3-deoxy-α-D-glucopyranosyl chloride (3.9 gm.) was dissolved in dry benzene (100 ml.) and concentrated to 50 m. The solutions were combined, collidine (0.6 gm.) was added and the mixture was stirred under anhydrous conditions at 45°–50° for 18 hours. After filtration and evaporation of the solvent, the residue was chromatographed on a column of silica gel using 0.5% methanol in chloroform as eluant. A mixture of isomeric adducts (3.5 gm.) was obtained including O-[3-acetamido-3-deoxy-2,4,6-tri-O-benzyl-α/-D-glucopyranosyl-(1 → 6)]-1,3,2',6'-tetra-N-benzyloxycarbonylgentamine $C_1$. The mixture had m.p. 185°–187° $[\alpha]_D$+ 55°; [Found: C, 67.53; H, 6.55; N, 5.18: $C_{75}H_{85}N_5O_{17}$ requires C, 67.8; H, 6.4; N, 6.3%]. Ammonia (250 ml.) was distilled from sodium into a solution of the adduct mixture to which sodium (2 gm.) was then added in pieces. After 3 hours, the excess sodium was destroyed by the addition of water. The solvent was allowed to evaporate under a stream of nitrogen over 48 hours to hydrolyze the N-acetate. Water was added and the solution was neutralized with Amberlite IRC50 resin (H $^+$ form) and the slurry was poured into a column and washed with water. Elution with 1.5N ammonium hydroxide followed by lyophilization of the eluant gave a solid residue (1.5 gm.) which was chromatographed on a silica gel column using chloroform-methanol-concentrated ammonium hydroxide 1:1:1 (lower phase). O-[3-Amino-3-deoxy-α-D-glucopyranosyl-(1 → 6)] gentamine $C_1$(0.5 gm.) was obtained. It had $[\alpha]_D$ + 107.2° ($H_2O$); $[\theta]_{290}$+ 2,140 (TACu), + 1,790 (Cupra A); m/e 480 ($M^+$+1), 479 ($M^+$); δ($D_2O$), 0.95 (3H, d, J=6.5Hz, 6'-$CH_3$), 2.2 (s, 3H, H—$CH_3$), 4.96 (1H, d, J=3.5Hz, H-1''), 5.05 ppm. (1H, d, J=3.5Hz, H-1').

By substituting the 1,3,2',6'-tetra-N-benzyloxycarbonylgentamine $C_1$ with equivalent amounts of 1,3,2',-6'-tetra-N-benzyloxycarbonyl gentamine $C_2$, 1,3,2',-6'-tetra-N-benzyloxycarbonyl gentamine $C_{2b}$, and 1,3,2',6'-tetra-N-benzyloxycarbonyl gentamine $C_{1a}$ and by following substantially the same procedure of this example there is produced O-[3-amino-3-deoxy-α-D-glucopyranosyl-(1 → 6)] gentamine $C_2$, O-[3-amino-3-deoxy-α-D-glucopyranosyl-(1 → 6)] gentamine $C_{2b}$, and O-[3-amino-3-deoxy-α-D-glucopyranosyl-(1 → 6)] gentamine $C_{1a}$, respectively. Similarly, by substituting the 3-acetamido-2,4,6-tri-O-benzyl-3-deoxy-α-D-glucopyranosyl chloride with equivalent amounts of 3-(N-methylacetamido)-2,4,6-tri-O-benzyl-3-deoxy-α-D-glucopyranosyl chloride,
3-acetamido-2,4,6-tri-O-benzyl-3-deoxy-α-D-galactopyranosyl chloride,
3-(N-methylacetamido)-2,4,6-tri-O-benzyl-3-deoxy-α-D-galactopyranosyl chloride,
3-acetamido-2,4-di-O-benzyl-3-deoxy-α-D-fucopyranosyl chloride,
3-(N-methylacetamido)-2,4-di-O-benzyl-3-deoxy-α-D-fucopyranosyl chloride,
3-acetamido-3,6-dideoxy-2,4-di-O-benzyl-α-D-glucopyranosyl chloride,
3-(N-methylacetamido)-3,6-dideoxy-2,4-di-O-benzyl-α-D-glucopyranosyl chloride,
3-acetamido-2,4-di-O-benzyl-3-deoxy-α-D-xylopyranosyl chloride,
3-(N-methylacetamido)-2,4-di-O-benzyl-3-deoxy-α-D-xylopyranosyl chloride,
3-acetamido-2,4-di-O-benzyl-3-deoxy-β-L-arabinopyranosyl chloride, or
3-(N-methylacetamido)-2,4-O-benzyl-3-deoxy-β-L-arabinopyranosyl chloride (or the corresponding bromides of the foregoing) and by reacting said chlorides or bromides with any of the 1,3,2',6'-tetra-N-benzyloxycarbonyl gentamine $C_1$, 1,3,2',6'-tetra-N-benzyloxycarbonyl gentamine $C_2$, 1,3,2',6'-tetra-N-benzyloxycarbonyl gentamine $C_{1a}$, or 1,3,2',6'-tetra-N-benzyloxycarbonyl gentamine $C_{2b}$, according to the procedure of the above example (with, of course, expected minor variations, e.g. solvents) there is produced O-[3-(N-methylamino)-3-deoxy-α-D-glucopyranosyl-(1 → 6)] gentamine $C_1$,
O-[3-(N-methylamino)-3-deoxy-α-D-glucopyranosyl-(1 → 6)] gentamine $C_2$,
O-[3-(N-methylamino)-3-deoxy-α-D-glucopyranosyl-(1 → 6)] gentamine $C_{1a}$,
O-[3-(N-methylamino)-3-deoxy-α-D-glucopyranosyl-(1 → 6)] gentamine $C_{2b}$,
O-[3-amino-3-deoxy-α-D-galactopyranosyl-(1 → 6)] gentamine $C_1$,
O-[3-amino-3-deoxy-α-D-galactopyranosyl-(1 → 6)] gentamine $C_2$,
O-[3-amino-3-deoxy-α-D-galactopyranosyl-(1 → 6)] gentamine $C_{1a}$,
O-[3-amino-3-deoxy-α-D-galactopyranosyl-(1 → 6)] gentamine $C_{2b}$,
O-[3-(N-methylamino)-3-deoxy-α-D-galactopyranosyl-(1 → 6)] gentamine $C_1$, O-[3-(N-methylamino)-3-deoxy-α-D-galactopyranosyl-(1 → 6)] gentamine $C_2$,
O-[3-(N-methylamino)-3-deoxy-α-D-galactopyranosyl-(1 → 6)] gentamine $C_{1a}$,
O-[3-(N-methylamino)-3-deoxy-α-D-galactopyranosyl-(1 → 6)] gentamine $C_{2b}$,
O-[3-amino-3-deoxy-α-D-fucopyranosyl-(1 → 6)] gentamine $C_1$,
O-[3-amino-3-deoxy-α-D-fucopyranosyl-(1 → 6)] gentamine $C_2$,
O-[3-amino-3-deoxy-α-D-fucopyranosyl-(1 → 6)] gentamine $C_{1a}$,
O-[3-amino-3-deoxy-α-D-fucopyranosyl-(1 → 6)] gentamine $C_{2b}$,
O-[3-(N-methylamino)-3-deoxy-α-D-fucopyranosyl-(1 → 6)] gentamine $C_1$,
O-[3-(N-methylamino)-3-deoxy-α-D-fucopyranosyl-(1 → 6)] gentamine $C_2$,
O-[3-(N-methylamino)-3-deoxy-α-D-fucopyranosyl-(1 → 6)] gentamine $C_{1a}$,
O-[3-(N-methylamino)-3-deoxy-α-D-fucopyranosyl-(1 → 6)] gentamine $C_{2b}$,
O-[3-amino-3,6-dideoxy-α-D-glucopyranosyl-(1 → 6)] gentamine $C_1$,
O-[3-amino-3,6-dideoxy-α-D-glucopyranosyl-(1 → 6)] gentamine $C_2$,
O-[3-amino-3,6-dideoxy-α-D-glucopyranosyl-(1 → 6)] gentamine $C_{1a}$,
O-[3-amino-3,6-dideoxy-α-D-glucopyranosyl-(1 → 6)] gentamine $C_{2b}$,
O-[3-(methylamino)-3,6-dideoxy-α-D-glucopyranosyl-(1 → 6)] gentamine $C_1$,
O-[3-(methylamino)-3,6-dideoxy-α-D-glucopyranosyl-(1 → 6)] gentamine $C_2$,
O-[3-(methylamino)-3,6-dideoxy-α-D-glucopyranosyl-(1 → 6)] gentamine $C_{1a}$,
O-[3-(methylamino)-3,6-dideoxy-α-D-glucopyranosyl-(1 → 6)] gentamine $C_{2b}$,
O-[3-amino-3-deoxy-α-D-xylopyranosyl-(1 → 6)] gentamine $C_1$,
O-[3-amino-3-deoxy-α-D-xylopyranosyl-(1 → 6)] gentamine $C_2$,
O-[3-amino-3-deoxy-α-D-xylopyranosyl-(1 → 6)] gentamine $C_{1a}$,
O-[3-amino-3-deoxy-α-D-xylopyranosyl-(1 → 6)] gentamine $C_{2b}$,
O-[3-(N-methylamino)-3-deoxy-α-D-xylopyranosyl-(1 → 6)] gentamine $C_1$,
O-[3-(N-methylamino)-3-deoxy-α-D-xylopyranosyl-(1 → 6)] gentamine $C_2$,
O-[3-(N-methylamino)-3-deoxy-α-D-xylopyranosyl-(1 → 6)] gentamine $C_{1a}$,
O-[3-(N-methylamino)-3-deoxy-α-D-xylopyranosyl-(1 → 6)] gentamine $C_{2b}$,
O-[3-amino-3-deoxy-β-L-arabinopyranosyl-(1 → 6)] gentamine $C_1$,
O-[3-amino-3-deoxy-β-L-arabinopyranosyl-(1 → 6)] gentamine $C_2$,
O-[3-amino-3-deoxy-β-L-arabinopyranosyl-(1 → 6)] gentamine $C_{1a}$,
O-[3-amino-3-deoxy-β-L-arabinopyranosyl-(1 → 6)] gentamine $C_{2b}$,
O-[3-(methylamino)-3-deoxy-β-L-arabinopyranosyl-(1 → 6)] gentamine $C_1$,
O-[3-(methylamino)-3-deoxy-β-L-arabinopyranosyl-(1 → 6)] gentamine $C_2$,
O-[3-(methylamino)-3-deoxy-β-L-arabinopyranosyl-(1 → 6)] gentamine $C_{1a}$, and
O-[3-(methylamino)-3-deoxy-β-L-arabinopyranosyl-(1 → 6)] gentamine $C_{2b}$.

EXAMPLE 6:

O-[3-Amino-3-deoxy-α-D-glucopyranosyl-(1 → 6)] gentamine $C_1$ 1,3,2',6'-Tetra-N-benzyloxycarbonyl gentamine $C_1$ (1.0 gm.) and 3-acetamido-4,6-di-0-acetyl-2,3-dideoxy-2-nitroso-α-D-arabinopyranosyl chloride (0.73 gm.) were stirred in dry dimethylformamide (9 ml.) at 25° for 24 hours. The reaction mixture was poured into water and the precipitate was filtered, dried and chromatographed on a silica gel column using 1% ethanol in chloroform to give crude 0-[3-acetamido-4,6-di-0-acetyl-2,3-dideoxy-2-oximino-α-D-arabinopyranosyl-(1 → 6)]-1,3,2',6'-tetra-N-benzyloxycarbonyl gentamine $C_1$ (0.45 gm.) as an amorphous solid. The crude adduct (0.3 gm.), acetaldehyde (4ml.), acetonitrile (3 ml.), tetrahydrofuran (1 ml.) and 1N aqueous hydrochloric acid (1ml.) were combined and stirred at room temperature for 18 hours. The acetaldehyde was removed by evaporation and the residue was partitioned between water and ethyl acetate. The organic phase was dried and evaporated to give a solid residue which was dissolved in dioxane-water (3:1) (3 ml.) and cooled to 0°. Sodium borohydride (50 mg.) in dioxane-water (3:1) (2 ml.) was added at 0°. After 1½ hours glacial acetic acid was added to destroy the excess sodium borohydride and the solvent was removed under reduced pressure. The solid residue in tetrahydrofuran (3 ml.) was treated with liquid ammonia (30 ml.) and sodium pieces (0.3 gm.). After 2 hours water was added to destroy the excess reagent and the solvents were allowed to evaporate over 18 hours. Water (1 ml.) was added and the solution was heated at 100° for 4 hours, cooled and adsorbed onto excess Amberlite IRC 50 resin. The slurry was poured into a column and washed with water. Elution with 1.5N ammonium hydroxide, and concentration of the eluant to a small volume was followed by passage down a column of Amberlite IR 401S (OH⁻) resin and lyophilization. 0-[3-Amino-3-deoxy-α-D-glucopyranosyl-(1 → 6)] gentamine $C_1$ was obtained as an amorphous solid (30 mg.). (Physical data as in example 5).

By substituting the 3-acetamido-4,6-di-0-acetyl-2,3-dideoxy-2-nitroso-α-D-arabinopyranosyl chloride with equivalent amounts of 3-(N-methylacetamido)-4,6-di-0-acetyl-2,3-dideoxy-2-nitroso-α-D-arabinopyranosyl chloride,
3-acetamido-4,6-di-0-acetyl-2,3-dideoxy-2-nitroso-α-D-lyxopyranosyl chloride,
3-(N-methylacetamido)-4,6-di-0-acetyl-2,3-dideoxy-2-nitroso-α-D-lyxopyranosyl chloride,
3-acetamido-4-0-acetyl-2,3,6-tri-deoxy-2-nitroso-α-D-lyxopyranosyl chloride,
3-(N-methylacetamido)-4-0-acetyl-2,3,6-tri-deoxy-2-nitroso-α-D-lyxopyranosyl chloride,
3-acetamido-4-0-acetyl-2,3-dideoxy-2-nitroso-α-D-threopyranosyl chloride,
3-(N-methylacetamido)-4-0-acetyl-2,3-dideoxy-2-nitroso-α-D-threopyranosyl chloride,
3-acetamido-4-0-acetyl-2,3-dideoxy-2-nitroso-α-L-erythropyranosyl chloride,
3-(N-methylacetamido)-4-0-acetyl-2,3-dideoxy-2-nitroso-α-L-erythropyranosyl chloride,
3-acetamido-4-0-acetyl-2,3,6-trideoxy-2-nitroso-α-D-arabinopyranosyl chloride, 3-(N-methylacetamido)-4-0-acetyl-2,3,6-trideoxy-2-nitroso-α-D-arabinopyranosyl chloride, and by following the foregoing example, there is produced the corresponding gentamine $C_1$ compounds, and by also substituting the corresponding gentamine $C_2$, gentamine $C_{1a}$ and gentamine $C_{2b}$ reactants with the foregoing 2-nitroso-monosaccharide reactants, there is produced the corresponding gentamine $C_2$, gentamine $C_{1a}$, and gentamine $C_{2b}$ pseudotrisaccharides, i.e.

0-[3-(N-methylamino)-3-deoxy-α-D-glucopyranosyl-(1 → 6)] gentamine $C_1$,
0-[3-(N-methylamino)-3-deoxy-α-D-glucopyranosyl-(1 → 6)] gentamine $C_2$,
0-[3-(N-methylamino)-3-deoxy-α-D-glucopyranosyl-(1 → 6)] gentamine $C_{1a}$,
0-[3-(N-methylamino)-3-deoxy-α-D-glucopyranosyl-(1 → 6)] gentamine $C_{2b}$,
0-[3-amino-3-deoxy-α-D-glucopyranosyl-(1 → 6)] gentamine $C_2$,
0-[3-amino-3-deoxy-α-D-glucopyranosyl-(1 → 6)] gentamine $C_{1a}$,
0-[3-amino-3-deoxy-α-D-glucopyranosyl-(1 → 6)] gentamine $C_{2b}$,
0-[3-amino-3-deoxy-α-D-galactopyranosyl-(1 → 6)] gentamine $C_1$,
0-[3-amino-3-deoxy-α-D-galactopyranosyl-(1 → 6)] gentamine $C_2$,
0-[3-amino-3-deoxy-α-D-galactopyranosyl-(1 → 6)] gentamine $C_{1a}$,
0-[3-amino-3-deoxy-α-D-galactopyranosyl-(1 → 6)] gentamine $C_{2b}$,
0-[3-(N-methylamino)-3-deoxy-α-D-galactopyranosyl-(1 → 6)] gentamine $C_1$,
0-[3-(N-methylamino)-3-deoxy-α-D-galactopyranosyl-(1 → 6)] gentamine $C_2$,
0-[3-(N-methylamino)-3-deoxy-α-D-galactopyranosyl-(1 → 6)] gentamine $C_{1a}$,
0-[3-(N-methylamino)-3-deoxy-α-D-galactopyranosyl-(1 → 6)] gentamine $C_{2b}$,
0-[3-amino-3-deoxy-α-D-fucopyranosyl-(1 → 6)] gentamine $C_1$,
0-[3-amino-3-deoxy-α-D-fucopyranosyl-(1 → 6)] gentamine $C_2$,
0-[3-amino-3-deoxy-α-D-fucopyranosyl-(1 → 6)] gentamine $C_{1a}$,
0-[3-amino-3-deoxy-α-D-fucopyranosyl-(1 → 6)] gentamine $C_{2b}$,
0-[3-(N-methylamino)-3-deoxy-α-D-fucopyranosyl-(1 → 6)] gentamine $C_1$,
0-[3-(N-methylamino)-3-deoxy-α-D-fucopyranosyl-(1 → 6)] gentamine $C_2$,
0-[3-(N-methylamino)-3-deoxy-α-D-fucopyranosyl-(1 → 6)] gentamine $C_{1a}$,
0-[3-(N-methylamino)-3-deoxy-α-D-fucopyranosyl-(1 → 6)] gentamine $C_{2b}$,
0-[3-amino-3-deoxy-α-D-xylopyranosyl-(1 → 6)] gentamine $C_1$,
0-[3-amino-3-deoxy-α-D-xylopyranosyl-(1 → 6)] gentamine $C_2$,
0-[3-amino-3-deoxy-α-D-xylopyranosyl-(1 → 6)] gentamine $C_{1a}$,
0-[3-amino-3-deoxy-α-D-xylopyranosyl-(1 → 6)] gentamine $C_{2b}$,
0-[3-(N-methylamino)-3-deoxy-α-D-xylopyranosyl-(1 → 6)] gentamine $C_1$,
0-[3-(N-methylamino)-3-deoxy-α-D-xylopyranosyl-(1 → 6)] gentamine $C_2$,
0-[3-(N-methylamino)-3-deoxy-α-D-xylopyranosyl-(1 → 6)] gentamine $C_{1a}$,
0-[3-(N-methylamino)-3-deoxy-α-D-xylopyranosyl-(1 → 6)] gentamine $C_{2b}$,
0-([3-amino-3-deoxy-α-L-arabinopyranosyl-(1 → 6)] gentamine $C_1$,
0-[3-amino-3-deoxy-α-L-arabinopyranosyl-(1 → 6)] gentamine $C_2$,
0-[3-amino-3-deoxy-α-L-arabinopyranosyl-(1 → 6)] gentamine $C_{1a}$,
0-[3-amino-3-deoxy-α-L-arabinopyranosyl-(1 → 6)] gentamine $C_{2b}$,
0-[3-(N-methylamino)-3-deoxy-β-L-arabinopyranosyl-(1 → 6)] gentamine $C_1$,
0-[3-(N-methylamino)-3-deoxy-β-L-arabinopyranosyl-(1 → 6)] gentamine $C_2$,
0-[3-(N-methylamino)-3-deoxy-α-L-arabinopyranosyl-(1 → 6)] gentamine $C_{1a}$,
0-[3-(N-methylamino)-3-deoxy-α-L-arabinopyranosyl-(1 → 6)] gentamine $C_{2b}$,
0-[3-amino-3,6-dideoxy-α-D-glucopyranosyl-(1 → 6)] gentamine $C_1$,
0-[3-amino-3,6-dideoxy-α-D-glucopyranosyl-(1 → 6)] gentamine $C_2$,
0-[3-amino-3,6-dideoxy-α-D-glucopyranosyl-(1 → 6)] gentamine $C_{1a}$,
0-[3-amino-3,6-dideoxy-α-D-glucopyranosyl-(1 → 6)] gentamine $C_{2b}$,
0-[3-(N-methylamino)-3,6-dideoxy-α-D-glucopyranosyl-(1 → 6)] gentamine $C_1$,
0-[3-(N-methylamino)-3,6-dideoxy-α-D-glucopyranosyl-(1 → 6)] gentamine $C_2$,
0-[3-(N-methylamino)-3,6-dideoxy-α-D-glucopyranosyl-(1 → 6)] gentamine $C_{1a}$,
0-[3-(N-methylamino)-3,6-dideoxy-α-D-glucopyranosyl-(1 → 6)] gentamine $C_{2b}$.

EXAMPLE 7:
6-0-[3-Amino-3-deoxy-α-D-glucopyranosyl] gentamine $C_1$ 1,3,2′,6′-Tetra-N-benzyloxycarbonylgentamine $C_1$ (8.54 g. in dry methylene chloride (200 ml.) is treated with 3-acetamido-3-deoxy-2,4,6-tri-0-benzyl-α-D-glucopyranosyl chloride (7.64 g.), dry tetrabutyl ammonium bromide (10 g.) and diisopropylmethylamine (1.725 g.). The mixture is stirred and heated under reflux for 48 hours. The reaction mixture is diluted with methylene chloride (300 ml.), the solution extracted twice with sodium bicarbonate solution, separated, and the organic layer dried and evaporated. The residue is chromatographed as described in Example 5 to give 6-0-[3-acetamido-3-deoxy-2,4,6-tri-0-benzyl-α-D-glucopyranosyl]-1,3,2′,6′-tetra-N-benzyloxycarbonylgentamine $C_1$. This product is then deblocked as described in Example 5 to give the title compound 6-0-[3-amino-3-deoxy-α-D-glucopyranosyl] gentamine $C_1$.

Other 6-0-aminoglycosylgentamines are prepared in similar manner.

EXAMPLE 8:
The preparation of nitroso dimers for the Lemieux process.
3-Acetamido-4,6,-di-0-acetyl-2,3-dideoxy-2-nitroso-α-D-arabinopyranosyl chloride.

Add a solution of 3-acetamido-3-deoxy-2,4,6-tri-0-acetyl-α-D-glucopyranosyl bromide (4.2 g.) in glacial acetic acid (30 ml.) dropwise to a stirred mixture of zinc dust in 50% aqueous acetic acid at 0°–4°. Stir at this temperature until thin layer chromatography indicates substantially complete consumption of starting material. Filter the mixture, evaporate the filtrate in vacuo to an oil, and triturate the oil several times with dichloromethane. Evaporate the combined extracts to dryness. Dissolve the residue in pyridine (10 ml.) and add acetic anhydride (2 ml.). After standing for 1 hour at room temperature, remove the solvents in vacuo and chromatograph the residue over silica gel using a mixture of benzene and acetone (9:1) as eluant. Combine the like fractions of the major product to give 3-acetamido-3-deoxy-4,6-di-0-acetyl-D-glucal (1.5 g.), m.p. 145°–151°, $[\alpha]_D + 65°$. Found: C, 52.8; H, 6.4; N, 5.1. $C_{12}H_{17}NO_6$ requires C, 53.1; H, 6.3; N, 5.2%.

Dissolve the D-glucal (1.2 g.) in reagent grade ethyl acetate (10 ml.) in a flask protected from moisture and equipped with gas inlet and outlet tubes. Pass nitrogen through the solution whilst cooling it to −5°. Change the gas to a slow stream of nitrosyl chloride. After excess nitrosyl chloride has been introduced, as indicated by the dark brown color, the gas stream is reverted to nitrogen. After reaction is complete, remove the solvent under reduced pressure at 40° to obtain the title compound (yield 70–90%). The material can be used directly in condensation with gentamine derivatives without further purification.

In similar manner other nitroso-chloro-sugar derivatives are prepared for use in the Lemieux reaction.

In general, the novel pseudotrisaccharides of this invention may be used to treat susceptible microbial infestations, the antimicrobial activity being readily ascertained by standard in vivo and in vitro tests well-known to the microbiologists. Typically the compounds of this invention exert significant broad spectrum antibacterial activity against gram negative and gram positive organisms, including those organisms which are resistant to treatment with other aminoglycosides, e.g. kanamycin.

A biological profile of a compound of this invention (6-0-[3-amino-3-deoxy-α-D-galactopyranosyl] gentamine $C_1$) is shown by the following chart.

| 6-O-[3-Amino-3-deoxy-α-D-galactopyranosyl] gentamine $C_1$ | | |
|---|---|---|
| Bacteria | 24 hours* | 48 hours* |
| Escherichia coli | | |
| W677/R55 | >25 | — |
| JR66 | >25 | — |
| JR88 | .075 | .075 |
| JR90 | .075 | .3 |
| R5/W677 | .075 | .075 |
| HL97/W677 | NG | .3 |
| St. Michael 589 | .3 | .3 |
| Baker 2 | .075 | .3 |
| F14-BK | .075 | .075 |
| LA290 R55 | .75 | >25 |
| 1574-1 | .075 | .3 |
| Swidinsky 4195 | >25 | — |
| ATCC 10536 | .075 | .075 |
| Pseudomonas | | |
| St. Michael 762 | .075 | .3 |
| St. Michael 1395 | .075 | .3 |
| NRRL 3223 | .075 | .075 |
| D-2 | .75 | >25 |
| Travers I | >25 | >25 |
| Stone 130 | .075 | .3 |
| Stone 138 | .075 | .3 |
| Stone 20 | .03 | .075 |
| Stone 39 | .075 | .3 |
| Shriners 10099 | >25 | — |
| Shriners 10006 | >25 | — |
| Capetown 18 | .075 | .3 |
| Shreveport 3796 | >25 | — |
| GN315 | .075 | .075 |
| Klebsiella | | |

-continued

| 6-O-[3-Amino-3-deoxy-α-D-galactopyranosyl] gentamine $C_1$ | | |
|---|---|---|
| Bacteria | 24 hours* | 48 hours* |
| Ad 17 | .075 | .075 |
| Ad 18 | .075 | .075 |
| Georgetown 3694 | >25 | — |
| Georgetown 3020 | >25 | — |
| Oklahoma 6 | >25 | — |
| Providence | | |
| 164 | >25 | — |
| Staphylococcus aureus | | |
| 209P | .03 | .075 |
| Wood | .03 | .075 |
| Ziegler | <.01 | .03 |
| 59N | <.01 | .075 |
| Streptococcus pyogenes | | |
| C | >25 | — |
| 27 | >25 | — |
| Group A Cruz | >25 | — |
| Group A Alvarez | >25 | — |
| Bacillus subtilis ATCC | | |
| 6623 | <.01 | <.01 |
| Proteus mirabilis | | |
| Harding | >25 | — |
| rettgeri Membel | >25 | — |
| rettgeri Anderson | >25 | — |
| Serratia | | |
| Dalton | .075 | .075 |
| Salmonella | | |
| Group B typhim | .075 | .075 |
| Candida albicans | | |
| Wisconsin | >25 | — |

*All results are in mcg/ml.

When used topically or locally, the novel compounds (I) may be formulated into dosage forms wherein the compounds represent about 1 to about 10% by weight. In those instances when the dosage form is intended for oral administration, the compounds of this invention may be administered so as to provide from about 10 to about 100 mg. per kilogram of body weight per day. If the parenteral route is employed a dosage range of about 2 to about 10 mg. per kilogram of body weight per day is employed.

The compounds of this invention may be formulated into dosage forms as the sole active ingredient or used in combination with other active ingredients.

The pharmaceutical formulations adapted for carrying the compound of this invention vary according to the mode and site of administration desired and the determination of the appropriate form is within the pharmaceutical arts. Exemplifying vehicles intended to carry this product for topical application are creams, lotions, solution, ointments, dusting powders, gels, suspensions, and aerosols, having propellants such as chlorofluoralkane mixtures, Freon 11 and Freon 12 mixture.

Other suitable dosage forms include vaginal suppositories, tablets, capsules, ophthalmic, otic and nasal solutions, shampoos and injectables. The compound of this invention may also be administered to animals by admixing it with their feed.

The following formulations are representative of pharmaceutical compositions containing compounds of this invention.

Formulation 1

| Parenteral Solution | mg/ml |
|---|---|
| O-[3-Amino-3-deoxy-α-D-glucopyranosyl-(1→6)] gentamine $C_1$ | 40 to 200 mg. |
| Methylparaben | 1.8 mg. |
| Propylparaben | 0.2 mg. |
| Water for Injection q.s. | 1.0 ml. |

Place 70% of the water for injection into a suitable mixing vessel and heat to 70°C. Add the methylparaben and propylparaben and mix until dissolved. Cool the above solution to 25°–30°C. Pass a stream of nitrogen gas through the solution. Add the 0-[3-amino-3-deoxy-α-D-glucopyranosyl-(1 → 6)] gentamine $C_1$ and mix until dissolved. Bring the solution to final volume. Pass the solution through a suitable sterilizing filter, employing appropriate aseptic techniques. Fill the solution into suitable sterile containers employing appropriate aseptic filling techniques.

Formulation 2

| Oral Syrup | Per Liter |
|---|---|
| 0-[3-Amino-3-deoxy-α-D-glucopyranosyl-(1→ 6)]gentamine $C_1$ | 100 g. |
| Standard Granulated Sugar | 550 g. |
| Sorbitol Solution | 200 g. |
| Preservatives, Sufficient | — |
| Purified Water, to make | 1.0 liter |

Add the 0-[3-amino-3-deoxy-α-D-glucopyranosyl-(1 → 6)] gentamine $C_1$, standard granulated sugar, sorbitol solution, preservatives to approximately 350 ml. of purified water contained in a suitable mixing vessel. Mix until a solution is obtained. Add sufficient purified water to make 1 liter. Pass solution through a suitable clarifying filter.

Formulation 3

| Topical Cream | Per Kg. |
|---|---|
| 0-[3-Amino-3-deoxy-α-D-glucopyranosyl-(1→ 6)]gentamine $C_1$ | 10 g. — 100 g. |
| Ethoxylated Cetyl/Stearyl Alcohol | 20 g. |
| Cetyl Alcohol | 35 g. |
| Stearyl Alcohol | 35 g. |
| Petrolatum | 200 g. |
| Mineral Oil | 50 g. |
| Buffers, Sufficient | — |
| Preservatives, Sufficient | — |
| Purified water, to make | 1.0 kg. |

Add the cetyl alcohol, stearyl alcohol, ethoxylated acetyl/stearyl alcohol, petralatum, and mineral oil to a suitable mixing vessel. Heat to 80°C to melt. Mix. Add the preservatives, buffers and 0-[3-amino-3-deoxy-α-D-gluocopyranosyl-(1 → 6)] gentamine $C_1$ in approximately 95% of the purified water heated to 80°C in a suitable mixing vessel. Mix. Add the melted wax phase to the aqueous phase and mix while cooling to approximately 40°C. Add sufficient purified water to make 1 kg. Mix until cool.

Formulation 4

| Topical Ointment | Per Kg. |
|---|---|
| 0-[3-Amino-3-deoxy-α-D-glucopyranosyl-(1 → 6)]gentamine $C_1$ | 10 g. — 100 g. |
| White Petrolatum, to make | 1.0 kg. |

Melt and heat the petrolatum to 50°C in a suitable mixing vessel. Remove a portion of the melted petrolatum and make a slurry of the 0-[3-amino-3-deoxy-α-D-glucopyranosyl-(1 → 6)] gentamine $C_1$. Pass the slurry through a suitable colloid mill and mill until a uniform dispersion is obtained. Add the milled slurry to the remainder of the melted petrolatum and mix until cool.

Formulation 5

| Tablets | Per Tablet |
|---|---|
| 0-[3-Amino-3-deoxy-α-D-glucopyranosyl-(1 → 6)]gentamine $C_1$ | 25.0 mg. |
| Lactose, Impalpable Powder | 190.0 mg. |
| Corn Starch | 25.0 mg. |
| Polyvinylpyrrolidone | 7.5 mg. |
| Magnesium Stearate | 2.5 mg. |
| Alcohol, SD 3A q.s. | |

Place the 0-[3-amino-3-deoxy-α-D-glucopyranosyl-(1 → 6)] gentamine $C_1$, lactose and the corn starch into a suitable mixing bowl and mix. Prepare a solution of the polyvinylpyrrolidone in alcohol. Use this solution to prepare a damp mass of the powders. Screen the damp mass to produce granules. Dry the granules. Reduce the dried granules to a specific particle size. Add the magnesium stearate (lubricant) mix and compress the granulation into tablets using suitable tableting equipment.

Formulation 6

| Hard Gelatin Capsules | Per Capsule |
|---|---|
| 0-[3-Amino-3-deoxy-α-D-glucopyranosyl-(1→ 6)]gentamine $C_1$ | 25.0 mg. |
| Lactose, Impalpable Powder | 224.0 mg. |
| Magnesium Stearate | 1.0 mg. |

Place the 0-[3-amino-3-deoxy-α-D-glucopyranosyl-(1 → 6)] gentamine $C_1$ and lactose into a suitable mixing bowl and mix. Pass the mixed powders through a mill. Add the mixed milled powders to a suitable mixing vessel and mix again. Pre-mix the magnesium stearate with a portion of the batch from above. Pass the pre-mixed magnesium stearate of the batch and mix. Fill into empty gelatin capsules using suitable encapsulating equipment.

I claim:

1. Compounds having the structural formula:

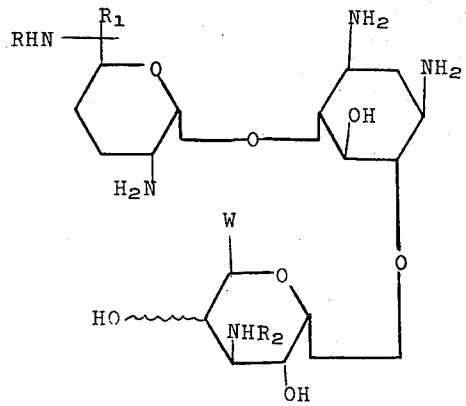

wherein each of R and $R_1$ represent hydrogen or methyl, $R_2$ is hydrogen or lower alkyl having less than 5 carbon atoms, and W represents hydrogen, methyl or hydroxymethyl, with the provisos that (a) when R, $R_1$ and $R_2$ are hydrogen, the 3-amino-3-deoxy sugar has other than the gluco-configuration, and (b) both R and $R_1$ must be hydrogen or methyl.

2. Compounds of claim 1 wherein R and $R_1$ are both methyl.

3. Compounds of claim 1 wherein R and $R_1$ are both hydrogen.

4. Compounds of claim 2 wherein W is hydrogen.

5. Compounds of claim 2 wherein W is methyl.

6. Compounds of claim 2 wherein W is $CH_2OH$.

7. Compounds of claim 3 wherein W is hydrogen.

8. Compounds of claim 3 wherein W is methyl.

9. Compounds of claim 3 wherein W is $CH_2OH$.

10. A compound of claim 2, said compound being 0-[3-amino-3-deoxy-α-D-glucopyranosyl-(1 → 6)] gentamine $C_1$.

11. A compound of claim 2, said compound being 0-[3-(N-methylamino)-3-deoxy-α-D-glucopyranosyl-(1 → 6)] gentamine $C_1$.

12. A compound of claim 2, said compound being 0-[3-amino-3-deoxy-α-D-galactopyranosyl-(1 → 6)] gentamine $C_1$.

13. A compound of claim 2, said compound being 0-[3-(N-methylamino)-3-deoxy-α-D-galactopyranosyl-(1 → 6) gentamine $C_1$.

14. A compound of claim 2, said compound being 0-[3-amino-3-deoxy-α-D-fucopyranosyl-(1 → 6)] gentamine $C_1$.

15. A compound of claim 2, said compound being 0-[3-(N-methylamino)-3-deoxy-α-D-fucopyranosyl-(1 → 6)] gentamine $C_1$.

16. A compound of claim 2, said compound being 0-[3-amino-3-deoxy-α-D-xylopyranosyl-(1 → 6)] gentamine $C_1$.

17. A compound of claim 2, said compound being 0-[3-(N-methylamino)-3-deoxy-α-D-xylopyranosyl-(1 → 6)] gentamine $C_1$.

18. A compound of claim 2, said compound being 0-[3-amino-3-deoxy-α-L-arabinopyranosyl-(1 → 6)] gentamine $C_1$.

19. A compound of claim 2, said compound being 0-[3-methylamino-3-deoxy-α-L-arabinopyranosyl-(1 → 6)] gentamine $C_1$.

20. A compound of claim 2, said compound being 0-[3-amino-3,6-dideoxy-α-D-glucopyranosyl-(1 → 6)] gentamine $C_1$.

\* \* \* \* \*